United States Patent
Albalat et al.

(10) Patent No.: US 8,350,092 B2
(45) Date of Patent: Jan. 8, 2013

(54) PROCESS OF RACEMISATION OF OPTICALLY ACTIVE ALPHA AMINOACETALS

(75) Inventors: Muriel Albalat, Coudoux (FR); Geraldine Primazot, Compiegne (FR); Didier Wilhelm, Issy les Moulineaux (FR); Jean-Claude Vallejos, La Ciotat (FR)

(73) Assignee: Clariant Specialty Fine Chemicals (France), Puteaux (FR)

( * ) Notice: Subject to any disclaimer, the term of this patent is extended or adjusted under 35 U.S.C. 154(b) by 459 days.

(21) Appl. No.: 12/601,067

(22) PCT Filed: May 21, 2008

(86) PCT No.: PCT/EP2008/056219
§ 371 (c)(1),
(2), (4) Date: Nov. 20, 2009

(87) PCT Pub. No.: WO2008/142088
PCT Pub. Date: Nov. 27, 2008

(65) Prior Publication Data
US 2010/0152490 A1    Jun. 17, 2010

(30) Foreign Application Priority Data
May 22, 2007   (FR) .................................... 07 55190

(51) Int. Cl.
*C07C 43/00*   (2006.01)
(52) U.S. Cl. ........................................................ 568/590
(58) Field of Classification Search ................... None
See application file for complete search history.

(56) References Cited

U.S. PATENT DOCUMENTS

| 4,769,486 A * | 9/1988 | Harada et al. ................. 562/401 |
| 5,476,964 A * | 12/1995 | House .......................... 560/254 |
| 6,670,486 B1 * | 12/2003 | Bakonyi et al. ................. 549/76 |
| 7,220,883 B2 | 5/2007 | Serradeil Albalat et al. |
| 2011/0034726 A1 | 2/2011 | Albalat et al. |

FOREIGN PATENT DOCUMENTS

| EP | 0249349 | 12/1987 |
| EP | 0291234 | 11/1988 |
| EP | 0367242 | 5/1990 |
| EP | 0374647 | 6/1990 |
| EP | 0779261 | 6/1997 |
| EP | 1527041 | 5/2004 |
| FR | 2843112 | 2/2004 |
| JP | 59 170058 | 9/1984 |
| WO | WO96/14857 | 5/1996 |
| WO | WO98/22496 | 5/1998 |
| WO | WO2004/013081 | 2/2004 |

OTHER PUBLICATIONS

International Search Report for PCT/EP2008/056219, dated Jul. 28, 2008.
Translation of Written Opinion of the Internatonal Searching Authority for PCT/EP2008/056219, dated Jul. 28, 2008.
International Search Report for PCT/EP2009/050665, dated Mar. 10, 2009.
Translation of International Preliminary Report on Patentability for PCT/EP2009/050665, dated Mar. 26, 2010.
English Abstract for JP 59 170058, Sep. 29, 1984.
English Abstract for EP 0374647, Jun. 27, 1990.
Tetrahedron (1974), 30(23/24), 4233-4237.
Guillaumie, et al., "Solid—phase synthesis of C—terminal peptide aldehydes from amino acetals anchored to a backbone amide linker (BAL) handle", Tetrahedron Lett., 2000, 41(32), 6131-6135.
Kurt Kahr, et al., "Katalytische Oxydation von primaren Aminen zu Oximen mit Wasserstoffperoxyd", Chemische Berichte., vol. 93, No. 1960, 1960, pp. 132-136.
J. Jurczak et al., Chem. Rev., (1989), 89 (1), 149-164.
M.T. Reetz, Angew Chem., Int. Ed. Engl., (1991), 30 (12), 1531-1546.
D. Enders et al., Angew. Chem., Int. Ed. Engl., (1993), 32 (3), pp. 418-421.
Chemical Abstracts, Heterocyclic Compounds, (1962), 3425.
J. Chem. Soc., 1957, 2146-2158.
J. Med. Chem., 1987, 30(1), 150-156.
J. Org. Chem., 1981, 46(8), 1575-1585.
Bioorg. & Med. Chem. Lett., 2002, 12(4), 701-704.
J. Heterocycl. Chem., 1978, 15(4), 665-670.

* cited by examiner

*Primary Examiner* — Karl J Puttlitz
(74) *Attorney, Agent, or Firm* — Tod A. Waldrop

(57) ABSTRACT

The invention relates to a process for preparing α-aminoacetals substantially in racemic form, comprising a step of oxidizing optically enriched α-aminoacetals to the corresponding oximes, in the presence of a catalyst, and a step of reducing the oximes thus obtained.

19 Claims, No Drawings

PROCESS OF RACEMISATION OF OPTICALLY ACTIVE ALPHA AMINOACETALS

The invention relates to a process for the racemization of optically active α-aminoacetals in order to obtain racemic α-aminoacetals.

More particularly, this process uses a derivation of the amine function of optically active α-aminoacetals in order to enable the racemization of α-aminoacetals under mild conditions.

Despite the progress of the past few years in asymmetrical synthesis, the resolving of racemic mixtures remains the approach most commonly used for the industrial synthesis of optically pure compounds, since it is often the most economical and the most practical means to be implemented for preparing pure enantiomers. The main drawback of such a process in relation to an enantioselective synthesis is that a theoretical optical yield equal to 50% with respect to the desired product is obtained. Thus, in order to make this type of process cost-effective, it is necessary to develop a method of racemization so as to recover the unwanted enantiomer by recycling of the racemic mixture to be resolved. In the development of an industrial resolving process, the economic stakes in terms of racemization are considerable, but said racemization often presents many difficulties: harsh operating conditions that are often necessary, the possible formation of decomposition products, too great a modification of the substrate to envisage direct recycling, which is reflected by additional synthesis steps, etc.

The literature makes reference to methods of racemization developed and applied generally to selecting a family of compounds, which reflects a limitation of the known racemization techniques used. Among the racemization methods most commonly used, mention may, by way of examples, be made of: racemization catalyzed by a base (for compounds having a sufficiently acidic hydrogen on the chiral centre), by an enzyme (which concerns essentially racemization of α-amino acids and derivatives), by an acid (for compounds having a tautomeric keto-enol form), racemization by formation of a Schiff's base-type intermediate with an aldehyde (technique developed for α-amino acids and derivatives) or else racemization by redox reactions (this concerns essentially chiral amines).

The families of compounds most widely studied and involved in the study of these racemization methods are: α-amino acids and derivatives thereof, amines, and to lesser degrees, alcohols and ether, acetate and alkoxy derivatives.

Unfortunately, most of the conventional methods of racemization described for the families of α-amino acids and derivatives (catalysis with a base or an acid, formation of a Schiff's base-type intermediate) or of chiral aromatic amines (catalysis with a base, reducing conditions), have not been efficient in the racemization of α-aminoacetals under mild operating conditions.

The technical problem to be solved therefore consists in providing a process for the racemization of optically active α-aminoacetals with a satisfactory yield using mild conditions, i.e., in particular, without impairing the acetal function, and processes for treating and recycling the racemic mixture in a new resolving process, which are easy to implement.

It has now been found that the combination of a step of oxidizing optically enriched α-aminoacetals to the corresponding oximes, in the presence of a catalyst, and of a step of reducing the oximes thus obtained makes it possible to solve the above problem.

A subject of the invention is therefore a process for preparing α-aminoacetals substantially in racemic form of formula (I)

in which:

R$_1$ and R$_2$, which may be identical or different, represent a linear or branched C$_1$-C$_{12}$ alkyl group, or else R$_1$ and R$_2$ are attached so as to form a 1,3-dioxolan-2-yl group which is unsubstituted or substituted on positions 4 and/or 5 with one or more linear or branched C$_1$-C$_6$ alkyl substituents, or a 1,3-dioxan-2-yl group which is unsubstituted or substituted on positions 4 and/or 5 and/or 6 with one or more linear or branched C$_1$-C$_6$ alkyl substituents;

R$_3$ represents a linear or branched C$_1$-C$_{12}$ alkyl group; a C$_3$-C$_{10}$ cycloalkyl group; a cycloalkylalkyl group in which the cycloalkyl and alkyl groups are as defined above; a heterocycloalkyl group containing 3 to 10 atoms; a heterocycloalkylalkyl group in which the heterocycloalkyl and alkyl groups are as defined above; a monocyclic, bicyclic or tricyclic C$_6$-C$_{14}$ aryl group; a heteroaryl group containing 5 to 14 atoms; an arylalkyl group or a heteroarylalkyl group, in which the aryl, heteroaryl and alkyl groups are as defined above; a C(=O)R$_4$ group in which R$_4$ represents an OR$_5$ group in which R$_5$ represents an H, a linear or branched C$_1$-C$_{12}$ alkyl group, a C$_3$-C$_{10}$ cycloalkyl group, a heterocycloalkyl group, an aryl group or a heteroaryl group as defined above, or R$_4$ represents an —NHR$_6$ group in which R$_6$ represents an H, a linear or branched C$_1$-C$_{12}$ alkyl group, a C$_3$-C$_{10}$ cycloalkyl group, a heterocycloalkyl group, an aryl group or a heteroaryl group as defined above; all the alkyl, cycloalkyl, cycloalkylalkyl, heterocycloalkyl, heterocycloalkylalkyl, aryl, heteroaryl, arylalkyl and heteroarylalkyl groups above being unsubstituted or substituted, the asterisk * signifies that the C atom is an asymmetrical carbon, by racemization of optically enriched α-aminoacetals of formula (R)-(I) or (S)-(I)

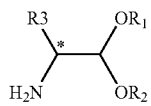

(R)-(I) or (S)-(I)

in which R$_1$, R$_2$, R$_3$ and the asterisk * are as defined for formula (I), characterized in that it comprises the steps consisting in:

oxidizing an optically enriched compound of formula (R)-(I) or (S)-(I) as defined above, in the presence of a catalyst, so as to obtain an oxime compound of formula (II)

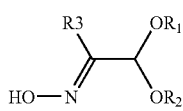

(II)

in which $R_1$, $R_2$ and $R_3$ are as defined above, and
reducing said compound of formula (II) to a compound of formula (I) as defined above, using a reducing agent.

In the present invention, the expression "racemization of optically enriched α-aminoacetals of formula (R)-(I) or (S)-(I)" means the racemization of the C atom bearing an asterisk *.

Preferably, use will be made of compounds of formula (R)-(I) or (S)-(I) in which:
- $R_1$ and $R_2$, which may be identical or different, represent a linear or branched $C_1$-$C_6$ alkyl group, in particular methyl or ethyl;
- $R_3$ represents a group chosen from a linear or branched $C_1$-$C_6$ alkyl group which is substituted or unsubstituted; a monocyclic, bicyclic or tricyclic $C_6$-$C_{14}$ aryl group, preferably phenyl, which is substituted or unsubstituted; an arylalkyl group in which the aryl and alkyl groups are as defined above; preferably benzyl, which is substituted or unsubstituted; a $C_3$-$C_{10}$ cycloalkyl group, preferably cyclohexyl, which is substituted or unsubstituted; a cycloalkylalkyl group in which the cycloalkyl group and the alkyl group are as defined above, preferably cyclobutylmethyl, which is substituted or unsubstituted.

Optional substituents of the groups $R_3$, $R_4$, $R_5$ and $R_6$ may be independently chosen from the groups halogen, OH (optionally protected, for example in the form of an ether with tetrahydropyran or in the form of an ester with the acetyl group), $NH_2$, $CO_2H$, $SO_3H$, $CF_3$, alkoxycarbonyl (or alkyl-O—CO—), amide, alkyl-N—CO—, alkylenedioxy (or —O-alkylene-O—), alkylsulphonyl (or alkyl-$SO_2$—), alkylsulphonylcarbamoyl (or alkyl-$SO_2$—NH—C(=O)—), —O-cycloalkyl, acyloxy, acylamino, alkylamino, dialkylamino, arylamino, diarylamino, arylalkylamino, oxo protected in the form of a cyclic or noncyclic ketal, formyl protected in the form of a cyclic or noncyclic acetal, aryloxy, alkyl, cycloalkyl, aryl, arylalkyl, heteroaryl and alkoxy.

In the products of Formulae (I), (S)-(I), (R)-(I) and (II) and also for the substituents, the groups indicated have the meanings which follow:
- the halogen group denotes fluorine, chlorine, bromine or iodine atoms;
- the alkyl group denotes a linear or branched $C_1$-$C_{12}$ group such as methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl, heptyl, octyl, nonyl, decyl, undecyl or dodecyl groups, linear or branched $C_1$-$C_6$ alkyl groups being preferred;
- the alkoxy group denotes a linear or branched $C_1$-$C_{12}$ group such as methoxy, ethoxy, propoxy, isopropoxy, linear, secondary or tertiary butoxy, pentoxy, hexoxy or heptoxy groups, linear or branched $C_1$-$C_6$ alkoxy groups being preferred;
- the cycloalkyl group denotes a monocyclic or bicyclic $C_3$-$C_{10}$ carbocyclic group such as cyclopropyl, cyclobutyl, cyclopentyl or cyclohexyl groups;
- the cycloalkylalkyl group denotes a group in which the cycloalkyl and alkyl residues have the meanings mentioned above, such as cyclopropylmethyl, cyclobutylmethyl, cyclopentylmethyl, cyclohexylmethyl, cycloheptylmethyl, cyclopropylethyl or cyclohexylethyl groups;
- the aryl group denotes an unsaturated monocyclic or bicyclic $C_6$-$C_{14}$ carbocyclic group, such as phenyl, naphthyl, indenyl or anthracenyl groups, particularly the phenyl group;
- the arylalkyl group denotes a group in which the aryl and alkyl residues have the meanings mentioned above, such as benzyl, phenylethyl, 2-phenylethyl or naphthylmethyl groups;
- the heterocycloalkyl group denotes a monocyclic or bicyclic carbocyclic group containing 3 to 10 atoms, interrupted with one or more heteroatoms, which may be identical or different, chosen from oxygen or nitrogen atoms, such as dioxolanyl, dioxanyl, oxiranyl, piperazinyl, piperidinyl, pyrrolidinyl, imidazolidinyl, pyrazolidinyl, morpholinyl or tetrahydrofuryl groups;
- the heterocycloalkylalkyl group denotes a group in which the heterocycloalkyl and alkyl residues have the meanings mentioned above;
- the heteroaryl group denotes a monocyclic, bicyclic or tricyclic, aromatic carbocyclic group containing 5 to 14 atoms, or a bicyclic carbocyclic group in which one of the rings is aromatic and the other ring is completely hydrogenated, or else a tricyclic carbocyclic group in which at least one of the rings is aromatic and the other ring(s) is (are) completely hydrogenated, said carbocyclic group being interrupted with one or more heteroatoms, which may be identical or different, chosen from oxygen or nitrogen atoms, such as furyl (for example, 2-furyl), pyrrolyl, oxazolyl, oxadiazolyl, 3- or 4-isoxazolyl, imidazolyl, pyrazolyl, isoxazolyl, pyridyl (for example, 2- or 3- or 4-pyridyl), pyrimidinyl, pyridazinyl, pyrazinyl, tetrazolyl, benzofuranyl, indolyl, purinyl, quinolyl, isoquinolyl, chromanyl or naphthyridinyl groups;
- the heteroarylalkyl group denotes a group in which the heteroaryl and alkyl residues have the meanings mentioned above;
- the alkyl-O—CO— group denotes a linear or branched $C_2$-$C_{12}$ group in which the alkyl group has the meaning indicated above;
- the alkylene group denotes a linear or branched $C_1$-$C_6$ divalent hydrocarbon-based group, such as methylene, ethylene, propylene or isopropylene;
- the —O-alkylene-O— group denotes a linear or branched $C_1$-$C_6$ group in which the alkylene group has the meaning indicated above;
- the alkyl-$SO_2$— group denotes a linear or branched $C_1$-$C_{12}$ group in which the alkyl group has the meaning indicated above;
- the alkylsulphonylcarbamoyl group denotes a linear or branched $C_2$-$C_{12}$ group in which the alkyl group has the meaning indicated above;
- the —O-cycloalkyl group denotes a group in which the cycloalkyl group has the meaning indicated above;
- the acyloxy group denotes an r-CO—O— group in which r represents an alkyl, cycloalkyl, heterocycloalkyl, aryl or heteroaryl group, these groups having the values indicated above, such as acetoxy or propionyloxy;
- the acylamino group denotes an r-CO—N— group in which r has the meaning indicated above, such as acetamido;
- the alkyl-N—CO— group denotes a group in which the alkyl group has the meaning indicated above;
- the alkylamino, dialkylamino, arylamino, diarylamino and arylalkylamino groups denote groups in which the alkyl and aryl groups have the meanings indicated above;

the aryloxy group denotes an aryl-O— group in which the aryl group has the meaning indicated above, such as phenoxy or naphthyloxy.

The expression "optically enriched" means that the compound of formula (R)-(I) or (S)-(I) has an enantiomeric excess relative to the other enantiomer within the range of from 1% to 100%, preferably within the range of from 50% to 100%, and more preferably within the range of from 70% to 100%.

The expression "substantially racemic" means that the enantiomeric excess is less than 20%, preferably less than 10%, more preferably less than 5%, and most particularly that there is no enantiomeric excess.

The expression "enantiomeric excess" is intended to mean the ratio of the excess of the desired enantiomer relative to the undesired enantiomer.

This ratio is calculated according to one of the following equations:

% ee.(R)=([R]−[S]/[R]+[S])×100%

% ee.(S)=([S]−[R]/[R]+[S])×100 in which:
% ee.(R) represents the enantiomeric excess of R isomer
% ee.(S) represents the enantiomeric excess of S isomer
[R] represents the concentration of R isomer, and
[S] represents the concentration of S isomer.

The process of the invention comprises an oxidation step. In general, inorganic or organic peroxides and also complexes containing said peroxides may be used as oxidizing agents. By way of example, mention may be made of aqueous hydrogen peroxide, sodium perborate, sodium percarbonate, urea-$H_2O_2$ complex or tert-butyl hydroperoxide, aqueous hydrogen peroxide being preferred.

The appropriate catalysts for the oxidizing step are most particularly chosen from alkali metal salts of metal oxides of tungsten, of molybdenum and of vanadium. By way of example, mention may be made of sodium tungstate, potassium tungstate, sodium molybdate, potassium molybdate, sodium vanadate and potassium vanadate, and mixtures thereof, and most particularly sodium tungstate in its dihydrate form ($Na_2WO_4.2H_2O$).

Other types of catalysts can be used, such as titanium silicalites (TS-1 and TS-2), peroxotungstophosphate and methyltrioxorhenium (MTO).

Preferred conditions for the oxidation step for forming the compound of formula (I) may be chosen from the following:
the oxidation is carried out in the presence of an aqueous solution of hydrogen peroxide, preferably a 30% solution, in an amount of between 1 and 10 molar equivalents, preferably 3 to 4 molar equivalents;
the catalyst, for example sodium tungstate dihydrate ($Na_2WO_4.2H_2O$), is present in an amount of between 1 and 30 mol %, and preferably 12 mol %;
the oxidation is carried out in an inert solvent or a mixture of inert solvents, such as water or alcohol or in a water/alcohol mixture, and preferably a mixture of water/methanol in equivalent amount;
the temperature is between −5° C. and 50° C., preferably about ambient temperature;
the duration is between 1 h and 48 h.

Under preferred conditions for carrying out the process according to the invention, the oxime derivative of formula (II) can be used in the reduction step without further purification.

The reduction can be carried out using metal hydrides such as, for example, sodium borohydride, lithium borohydride or lithium aluminium borohydride ($LiAlH_4$), or by catalytic hydrogenation such as hydrogenations in the presence of a supported noble metal (Pd—C/$H_2$ or Pt—C/$H_2$) or in the presence of Raney nickel (Ra—Ni/$H_2$).

Those skilled in the art are in a position to choose, by virtue of their general knowledge, the appropriate method of reduction according to the oxime derivative of formula (II).

Under preferred conditions for carrying out the step of reducing the compound of formula (II) so as to obtain the compound of formula (I) in substantially racemic form, said reduction is carried out by hydrogenation in the presence of Raney nickel under the following conditions:
the reaction is preferably carried out with an aqueous suspension of Raney nickel at 50%,
the amount of Raney nickel is between 1 and 10 molar equivalents of nickel atom, preferably 3 molar equivalents of nickel atom, relative to the oxime compound of formula (II),
the reaction is carried out in an inert solvent or a mixture of inert solvents, such as water or an alcohol or in a water/alcohol mixture, and preferably in ethanol,
the reaction is carried out under a hydrogen pressure of between 100 kPa and 5000 kPa of hydrogen, preferably under 2000 kPa of hydrogen,
the temperature is between 0° C. and 50° C., preferably around ambient temperature;
the reaction time is between 1 h and 48 h.

The optically enriched α-aminoacetals of formula (R)-(I) or (S)-(I) can be obtained by adapting methods known from the literature, for instance from α-amino acids, followed by formation of a Weinreb amide, reduction with a hydride and acetalization as described in Tetrahedron Lett., 2000, 41(32), 6131-6135, WO 9822496 and WO 9614857, or by reduction to an alcohol, reoxidation to an aldehyde and acetalization as described in Tetrahedron Lett., 2000, 41(32), 6131-6135, EP 291234 and EP 249349.

The asymmetrical reduction of optically active imines, described in EP 374647, can also be used. Other approaches by asymmetrical induction are also described, such as the SAMP/RAMP method (Angew. Chem. Int. Ed. Engl., (1993), 32(3), 418-421) or else the use of chiral aminotriazoles (FR 2843112).

In general, any known process for preparing an optically enriched α-aminoacetal is suitable for the invention, such as the Rosenmund reduction process described in particular in Tetrahedron (1974), 30(23/24), 4233-4237.

The following examples illustrate the invention in a non-limiting manner.

The optical enrichment of the α-aminoacetals (R)-(I) or (S)-(I) can be determined by chiral HPLC, either directly or on derivatives, preferably on carbamate derivatives of N-Cbz type (Cbz=benzyloxycarbonyl), of formula (III):

(III)

in which:
the asterisk * signifies that the C atom is an asymmetric carbon, and
$R_1$, $R_2$, and $R_3$ have the meaning indicated above.

Analyses by nuclear magnetic resonance (NMR) were carried out on a Brucker AC200 apparatus in the common deuterated solvents ($CDCl_3$, $DMSOd_6$, etc.). Gas chromatography (GC) analyses were carried out on a Varian 3900 apparatus (FID detection) with a Chrompack column (30 m/CP-SIL 8 CB-low bleed MS/1 μm/0.25 mm) and as method of analysis: $T°_{injector}$ 250° C./$T°_{detector}$ 300° C./oven programming: 80° C. for 1 min, then 15° C./min up to 300° C. and maintain at 300° C.

EXAMPLE 1

1-benzyl-2,2-dimethoxyethylamine $R_1=R_2=$methyl;$R_3=$benzyl) (formula (I):

1/Oxidation:
In a 50 ml three-necked flask equipped with a condenser, a dropping funnel, a magnetic stirrer and a thermometer, 0.62 g of optically enriched (R)-1-benzyl-2,2-dimethoxyethylamine (83% ee, determined by chiral HPLC analysis) (3.2 mmol, 1 mol. eq.) is dissolved, with stirring, in 10 g of $H_2O$. 0.08 g of sodium tungstate dihydrate (0.24 mmol, 7.5% mol. eq.) is introduced into this medium with stirring. The temperature of the medium is brought to 0° C. and a 30% aqueous solution of hydrogen peroxide (9.6 mmol, 3 mol. eq.) is then added dropwise. Once the addition is complete, the medium is left to stir and allowed to return to ambient temperature slowly. The stirring is continued overnight.
The reaction medium is washed with 8 ml of a saturated aqueous solution of $Na_2SO_3$ and extracted with $CH_2Cl_2$. After concentrating the organic phase, a mass of 0.52 g of 1,1-dimethoxy-3-phenylpropan-2-one oxime is obtained (yellow oil) (yield$_{crude}$=78%).
Empirical formula: $C_{11}H_{15}NO_3$
Molar mass: 209.25 g.mol$^{-1}$
GC analyses: $t_r$=15 min
NMR (200 MHz/CDCl$_3$):
$^1$H NMR: δ 3.2 (s, 6H, CH$_3$); 3.65 (s, 2H, CH$_2$); 4.58 (s, H, CH) and 7.1-7.35 (m, 5H, H$_{aromatic}$) ppm.
$^{13}$C NMR: δ 30.15 (CH$_2$); 54.2 (CH$_3$); 103.4 (CH); 126.17-128.22-129.4 (CH$_{aromatic}$); 136.6 (C$_{aromatic}$) and 155.7 (C=N) ppm.
2/Reduction:
In an autoclave reactor equipped with a mechanical stirrer, a thermocouple and a gas feed, 0.5 g of 1,1-dimethoxy-3-phenylpropan-2-one oxime (2.4 mmol, 1 mol.eq.) and an aqueous suspension of Raney nickel at 50% (2.5 g) are suspended in 64 g of 95% ethanol. After the reactor has been swept with nitrogen, the medium is placed under 5000 kPa (50 bar) of hydrogen with stirring at ambient temperature for 40 h. The progression of the reaction is followed by GC. The reduction is stopped once the disappearance of the starting product has been observed by GC.
The reaction medium is filtered through Célite®. The filtrate is concentrated, and 0.35 g of racemic 1-benzyl-2,2-dimethoxyethylamine is obtained (yellow-coloured oil, yield$_{crude}$=75%).
Chiral HPLC analysis is carried out in order to verify that the racemic mixture has been obtained.
Empirical formula: $C_{11}H_{17}NO_2$
Molar mass: 195.26 g.mol$^{-1}$
Boiling point: $B_p$=115-120° C. under 5 mmHg
GC analyses: $t_r$=13.65 min
EI MS m/z (% relative intensity): 164 (M-31, 11); 120 (M-75, 96); 104 (M-91, 39); 91 (62); 75 (100).

NMR (200 MHz/CDCl$_3$):
$^1$H NMR: δ 1.3 (s, 2H, NH$_2$); 2.5 (dd, 1H, syst AB CH$_2$); 3 (dd, 1H, syst AB CH$_2$); 3.15 (m, 1H, CH); 3.49 (s, 6H, CH$_3$); 4.14 (d, J=5.6 Hz, 1H, CH) and 7.19-7.4 (m, 6H, CH$_{aromatic}$) ppm.
$^{13}$C NMR: δ 38.7 (CH$_2$); 54.2 (CH); 55.05 and 55.19 (CH$_3$); 107.9 (CH); 126.3-128.3-128.56-129.1-129.4 (CH$_{aromatic}$) and 139.1 (C$_{aromatic}$) ppm.
Chiral HPLC analyses: Chiralcel® OD-H, 90/10 hexane/isopropanol; 1 ml/min; UV 254 nm and polarimeter
enantiomer (−) $t_R$=5.6 min
enantiomer (+) $t_R$=6.5 min

EXAMPLE 2

1-dimethoxymethyl-3-methylbutylamine $R_1=R_2=$methyl;$R_3=$isobutyl) (formula (I):

1/Oxidation:
In a 100 ml three-necked flask equipped with a condenser, a dropping funnel, a magnetic stirrer and a thermometer, 0.5 g of optically enriched 1-isobutyl-2,2-dimethoxyethylamine (76% ee) (3.1 mmol, 1 mol.eq) is dissolved, with stirring, in a methanol (1 g)/H$_2$O (1 g) mixture in the presence of sodium tungstate dihydrate (0.12 g, 0.36 mmol, 12% mol. %). A slight exotherm is observed when the reactants are brought into contact. The medium is left to stir at ambient temperature. A 30% aqueous solution of hydrogen peroxide (1.06 g, 9.3 mmol, 3 mol.eq.) is added, dropwise, to this reaction medium for approximately 1 h. A slight exotherm also occurs during the addition. Once this addition is complete, the medium is left to stir at ambient temperature for 1 h, and then methanol is added (≈3 ml) in order to obtain a homogeneous medium. The progression of the reaction is followed by GC analyses. The medium is treated once the disappearance of the starting α-aminoacetal has been observed by GC (approximately 5-7 h).
10 ml of methyl tert-butyl ether (MTBE) are added to the residue, followed by 8 ml of a saturated aqueous solution of Na$_2$SO$_3$. The aqueous phase is separated by settling out and extracted. The organic phase obtained is dried over MgSO$_4$ and concentrated. 0.4 g of 1,1-dimethoxy-4-methylpentan-2-one oxime is obtained (yellow oil) (yield$_{crude}$=70%).
Empirical formula: $C_8H_{17}NO_3$
Molar mass: 175.23 g.mol$^{-1}$
GC analyses: $t_r$=10.5 min
NMR (200 MHz/CDCl$_3$):
$^1$H NMR: δ 0.95 (m, 6H, CH$_3$); 2.15 (m, 1H, CH); 2.3 (m, 2H, CH$_2$); 3.4-3.45 (m, 6H, CH$_3$); and 4.7 (s, 1H, CH) ppm.
$^{13}$C NMR: δ 23.05 (CH$_3$); 26.2 (CH); 32.9 (CH$_2$); 54.43 (CH$_3$); 104.40 (CH) and 157.20 (C=N) ppm.
2/Reduction:
In an autoclave reactor equipped with a mechanical stirrer, a thermocouple and a gas feed, 3.28 g of 1,1-dimethoxy-4-methyl-pentan-2-one oxime (18.7 mmol, 1 mol.eq.) and 6.6 g of an aqueous suspension of Raney nickel at 50% (3 mol.eq. Ni) are suspended in 64 g of 95% ethanol. After the reactor has been swept with nitrogen, the medium is placed under 2000 kPa (20 bar) of hydrogen with stirring at ambient temperature. The progression of the reaction is followed by GC and the reduction is stopped once the disappearance of the starting product has been observed (15-24 h).

The reaction medium is filtered through Celite. The filtrate is concentrated. 2.30 g of racemic 1-dimethoxymethyl-3-methylbutylamine are obtained (colourless oil) (yield$_{crude}$=77%).

Empirical formula: $C_8H_{19}NO_2$
Molar mass: 161.25 g.mol$^{-1}$
Boiling point: $B_p$=75° C. under 10 mmHg
GC analyses: $t_r$=8.65 min
EI MS m/z (% relative intensity): 130 (M-31, 7); 86 (M-75, 100); 75 (67); 43 (80).
NMR (200 MHz/CDCl$_3$):
$^1$H NMR: δ 0.85 (dd, 6H, CH$_3$); 1.2 (m, 4H, CH$_2$+NH$_2$); 1.7 (m 1H, CH); 2.82 (m, 1H, CH); 3.33 (s, 3H, CH$_3$); 3.36 (s, 3H, CH$_3$) and 3.92 (d, J=5.6 Hz, 1H, CH) ppm.
$^{13}$C NMR: δ 21.5 (CH$_3$); 23.97 (CH$_3$); 24.5 (CH); 41.5 (CH$_2$); 50.6 (CH); 54.8 (CH$_3$); 55.2 (CH$_3$) and 108.9 (CH) ppm.

3/Determination of the Optical Purity

The optical purity is determined by chiral HPLC on the corresponding carbamate derivatives of formula (III), of N-Cbz type.

Empirical formula: $C_{16}H_{25}NO_4$
Molar mass: 295.38 g.mol$^{-1}$
GC analyses: $t_r$=18.1 min
NMR (200 MHz/CDCl$_3$):
$^1$H NMR: δ 0.84 (m, 6H, CH$_3$); 1.27 (m, 2H, CH$_2$); 1.59 (m, 1H, CH); 3.34 (s, 6H, CH$_3$); 3.8 (m, 1H, CH); 4.1 (s$_{distorted}$, 1H, CH); 4.75 (d, 1H, NH$_2$); 5.03 (s, 2H, CH$_2$) and 7.1-7.3 (m, 5H, H$_{aromatic}$) ppm.
$^{13}$C NMR: δ 21.82 (CH$_3$); 23.6 (CH$_3$); 24.59 (CH); 38.5 (CH$_2$); 50.8 (CH); 56.01 (CH$_3$); 56.16 (CH$_3$); 66.73 (CH$_2$); 106.63 (CH); 128.05-128.54-128.79 (CH$_{aromatic}$); 136.72 (C$_{aromatic}$) and 156.37 (C=O) ppm.
Chiral HPLC analysis: Chiralcel® OD-H, 90/10 hexane/isopropanol, 1 ml/min, UV 254 nm and polarimeter
enantiomer (−) $t_R$=4.8 min
enantiomer (+) $t_R$=7.9 min

COMPARATIVE EXAMPLE 1

In a 50 ml three-necked flask equipped with a thermometer, a magnetic stirrer and a condenser, 0.14 g of optically enriched (R)-1-benzyl-2,2-dimethoxyethylamine (91% ee, determined by chiral HPLC) (0.71 mmol, 1 mol.eq.) and 0.09 g of salicylaldehyde (0.71 mmol, 1 mol.eq.) are introduced into 1 g of toluene. This medium is left to stir at ambient temperature for 2-3 h. After concentrating, a crude mass of 0.21 g of 2-[(1-benzyl-2,2-dimethoxyethylimino)methyl]phenol is obtained.

In a 50 ml three-necked flask equipped with a thermometer, a magnetic stirrer and a condenser, the imine obtained above and 80 mg of potassium tert-butoxide ((CH$_3$)$_3$OK) (0.71 mmol, 1 mol.eq.) are introduced into 0.9 g of tetrahydrofuran (THF). This medium is left to stir at ambient temperature for 72 h and then a saturated aqueous solution of NH$_4$Cl is added. After separation by settling out, the organic phase is concentrated.

The chiral HPLC analysis of the residue obtained indicates an enantiomeric excess of 90%, which means that there is therefore no racemization of the starting α-aminoacetal.

The same result is observed using 3 mol.eq. of a 10% solution of sodium ethanoate base (EtONa) in THF.

COMPARATIVE EXAMPLE 2

In a 50 ml three-necked flask equipped with a thermometer, a magnetic stirrer and a condenser, 0.28 g of the imine obtained as above in Comparative Example 1 is introduced into 0.8 g of acetic acid. This medium is left to stir at ambient temperature for 24 h. Chiral HPLC analysis of a sample gives an enantiomeric excess of 90%. The medium is then heated at 50° C. for 6 h 30 and then at 80° C. for 7 h. Chiral HPLC analysis also gives an enantiomeric excess of 90%, which means that there is therefore no racemization.

The invention claimed is:

1. A process for preparing an α-aminoacetal substantially in racemic form of formula (I)

(I)

wherein:
R$_1$ and R$_2$, which may be identical or different, are a linear or branched C$_1$-C$_{12}$ alkyl group, or R$_1$ and R$_2$ are attached so as to form a 1,3-dioxolan-2-yl group which is unsubstituted or substituted on positions 4 and/or 5 with one or more linear or branched C$_1$-C$_6$ alkyl substituents, or a 1,3-dioxan-2-yl group which is unsubstituted or substituted on positions 4 and/or 5 and/or 6 with one or more linear or branched C$_1$-C$_6$ alkyl substituents;
R$_3$ is a linear or branched C$_1$-C$_{12}$ alkyl group; a C$_3$-C$_{10}$ cycloalkyl group; a cycloalkylalkyl group in which the cycloalkyl and alkyl groups are as defined above; a heterocycloalkyl group containing 3 to 10 atoms; a heterocycloalkylalkyl group in which the heterocycloalkyl and alkyl groups are as defined above; a monocyclic, bicyclic or tricyclic C$_6$-C$_{14}$ aryl group; a heteroaryl group containing 5 to 14 atoms; an arylalkyl group or a heteroarylalkyl group, in which the aryl, heteroaryl and alkyl groups are as defined above; a C(=O)R$_4$ group in which R$_4$ is an OR$_5$ group in which R$_5$ is a H, a linear or branched C$_1$-C$_{12}$ alkyl group, a C$_3$-C$_{10}$ cycloalkyl group, a heterocycloalkyl group, an aryl group or a heteroaryl group as defined above, or R$_4$ is a —NHR$_6$ group in which R$_6$ is a H, a linear or branched C$_1$-C$_{12}$ alkyl group, a C$_3$-C$_{10}$ cycloalkyl group, a heterocycloalkyl group, an aryl group or a heteroaryl group as defined above; wherein all the alkyl, cycloalkyl, cycloalkylalkyl, heterocycloalkyl, heterocycloalkylalkyl, aryl, heteroaryl, arylalkyl and heteroarylalkyl groups above may be unsubstituted or substituted,
the asterisk * signifies that the C atom is an asymmetrical carbon,
by racemization of an optically enriched α-aminoacetal of formula (R)-(I) or (S)-(I)

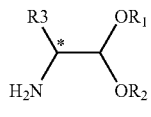

(R)-(I) or (S)-(I)

in which $R_1$, $R_2$, $R_3$ and the asterisk * are as defined for formula (I), comprising the steps of:

oxidizing an optically enriched compound of formula (R)-(I) or (S)-(I) as defined above, in the presence of a catalyst, so as to obtain an oxime compound of formula (II)

in which $R_1$, $R_2$ and $R_3$ are as defined above, and reducing the compound of Formula (II) to a compound of formula (I) as defined above, using a reducing agent.

2. A process according to claim 1, wherein:
$R_1$ and $R_2$, which may be identical or different, are a linear or branched $C_1$-$C_6$ alkyl group;
$R_3$ is a group chosen from a linear or branched $C_1$-$C_6$ alkyl group which is substituted or unsubstituted; a monocyclic, bicyclic or tricyclic $C_6$-$C_{14}$ aryl group which is substituted or unsubstituted; an arylalkyl group in which the aryl and alkyl groups as are defined above, which is substituted or unsubstituted; a $C_3$-$C_{10}$ cycloalkyl group which is substituted or unsubstituted; a cycloalkylalkyl group in which the cycloalkyl group and the alkyl group are as defined above, which is substituted or unsubstituted.

3. A process according to claim 1, wherein the oxidation step is carried out in the presence of an inorganic or organic peroxide.

4. A process according to claim 3, wherein the peroxide is chosen from aqueous hydrogen peroxide, sodium perborate, sodium percarbonate, urea-$H_2O_2$ complex or tert-butyl hydroperoxide.

5. A process according to claim 4, wherein the peroxide is aqueous hydrogen peroxide.

6. A process according to claim 3, wherein the peroxide is present in an amount of from 1 to 10 molar equivalents based on the optically enriched α-aminoacetals of formula (R)-(I) or (S)-(I).

7. A process according to claim 1, wherein the oxidation step is carried out in the presence of a catalyst chosen from the group consisting of alkali metal salts of metal oxides of tungsten, of molybdenum and of vanadium, or mixtures thereof, titanium silicalites, peroxotungstophosphate and methyltrioxorhenium.

8. A process according to claim 7, wherein the catalyst is chosen from the group consisting of sodium tungstate, potassium tungstate, sodium molybdate, potassium molybdate, sodium vanadate and potassium vanadate, and mixtures thereof.

9. A process according to claim 8, wherein the catalyst is sodium tungstate.

10. A process according to claim 7, wherein the catalyst is present in an amount of between 1 and 30 mol % based on the optically enriched α-aminoacetals of formula (R)-(I) or (S)-(I).

11. A process according to claim 1, wherein the reduction step is carried out using a metal hydride.

12. A process according to claim 11, wherein the reduction is carried out using sodium borohydride, lithium borohydride or lithium aluminium hydride.

13. A process according to claim 1, wherein the reduction step is carried out by hydrogenation in the presence of Raney nickel or a supported noble metal such as palladium-on-charcoal or platinum-on-charcoal.

14. A process according to claim 13, wherein the hydrogenation is carried out using Raney nickel.

15. A process according to claim 14, wherein the amount of Raney nickel is between 1 and 10 molar equivalents of nickel atom based on the amount of oxime compound of formula (II).

16. A process according to claim 14, wherein the amount of Raney nickel is 3 molar equivalents of nickel atom based on the amount of oxime compound of formula (II).

17. A process according to claim 7, wherein the catalyst is present in an amount of 12 mol % based on the optically enriched α-aminoacetals of formula (R)-(I) or (S)-(I).

18. A process according to claim 8, wherein the catalyst is sodium tungstate in its dihydrate form.

19. A process according to claim 3, wherein the peroxide is present in an amount of from 3 to 4 molar equivalents based on the optically enriched α-aminoacetals of formula (R)-(I) or (S)-(I).

* * * * *